United States Patent
Phelan et al.

(10) Patent No.: US 9,789,054 B1
(45) Date of Patent: Oct. 17, 2017

(54) METHOD AND COMPOSITION FOR MANAGING DAG ON HAIR

(71) Applicant: Empire Technology Development LLC, Wilmington, DE (US)

(72) Inventors: Gregory David Phelan, Cortland, NY (US); William Brenden Carlson, Shoreline, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 15/170,923

(22) Filed: Jun. 1, 2016

(51) Int. Cl.
  *A61K 8/898* (2006.01)
  *A61K 8/02* (2006.01)
  *A61K 8/41* (2006.01)
  *A61K 8/899* (2006.01)
  *A61Q 5/02* (2006.01)

(52) U.S. Cl.
  CPC .............. *A61K 8/898* (2013.01); *A61K 8/022* (2013.01); *A61K 8/41* (2013.01); *A61K 8/899* (2013.01); *A61Q 5/02* (2013.01); *A61K 2800/882* (2013.01)

(58) Field of Classification Search
  None
  See application file for complete search history.

(56) References Cited

U.S. PATENT DOCUMENTS

| 4,559,227 A | 12/1985 | Chandra et al. |
| 2014/0102469 A1* | 4/2014 | Loudon ............ A61Q 5/12 132/208 |
| 2014/0271750 A1* | 9/2014 | Schulze zur Wiesche .......... A61Q 5/12 424/401 |

OTHER PUBLICATIONS

Waghorn et al., "Dags in sheep: a look at faces and reasons for dag formation", Proceedings of the New Zealand Grassland Association 61: pp. 43-49 (1999).*
McKay, "Amodimethicone and other amine-funcitonalized silicons", Naturally Curly.com, Jul. 1, 2007, pp. 1-7.*
"Specialty silicones for age-defying hair shine," Dow Corning, http://www.dowcorning.com/content/personal/personalhair/age-defying-shine.aspx?, accessed on Dec. 17, 2015.
Flores, A., Silicones in Hair Products: Good or Bad?, http://blackhairmedia.com/hair-care/silicones-in-hair-products-good-or-bad, accessed on Dec. 17, 2015.
Harvey, V., "What Is Dimethicone?," accessed at http://www.wisegeek.org/what-is-dimethicone.htm, last modified on Apr. 21, 2015.
Pinksith, E., "Silicones in Hair Care. What You Need to Know,", http://www.pinksith.com/2013/05/silicones-in-hair-care-what-you-need-to.html, May 13, 2013.

* cited by examiner

*Primary Examiner* — Ernst V Arnold
*Assistant Examiner* — Kyung Sook Chang
(74) *Attorney, Agent, or Firm* — The Juhasz Law Firm, P.C.

(57) ABSTRACT

Technologies are generally described for a method and compounds for managing dag on hair. The method of managing dag on hair includes applying a low energy compound including a silicone and a terminal reactive group to the hair and applying a hair binding moiety to the hair for functionalizing the low energy compound, at its terminal reactive group, to bind to the hair. The applied low energy compound enables ease of removal of dag from the hair or mitigation of dag formation on the hair. The functionalized low energy compound may be made prior to the application to the hair.

17 Claims, 2 Drawing Sheets

METHOD AND COMPOSITION FOR MANAGING DAG ON HAIR

TECHNICAL FIELD

The present disclosure is directed generally towards a method and composition for managing dag on hair of animals, and more specifically towards enabling removal of dag from the hair or mitigation of dag formation on the hair of animals, especially livestock.

BACKGROUND

Dag, Daglock, or daggle-lock is a lumpy, dirty, or clotted hair mass that has accumulated on the skin or hide of livestock, such as cattle or sheep, and other animals. For example, dag may be a dangling or matted lock of fur, hair, or wool and may comprise feces or urine. For this disclosure, a dag is considered to be any foreign matter that clings to the skin, hide, hair, wool or other covering of an animal.

FIG. 1 shows a sheep having dag on its hair. The dags may be formed under typical farming conditions. Dag often forms with water, urine, and defecation, which may become a part of a concrete-like composite. The formation of dag may lead to an enhanced probability of disease as large amounts of bacteria may be introduced into the dag. Dag formation on cattle, or other livestock, and problems associated therewith, may be prevalent in many places. For example, Australian cattle are often exported in large ships. The dags may add considerable weight and should be removed from the cattle before boarding to prevent excess shipping weight, disease, and for passing inspection.

Dags adhered to the hair of livestock, may also represent a significant health problem for the animal processing industry. This may be especially true during seasonal periods of rain. Processing of "daggy" livestock at abattoirs may increase the risk that meat reaching the consumer is contaminated with pathogenic microorganisms.

Current methods for dag management may include dag removal which may induce stress in live animals at feedlots. This may have a detrimental effect on the quality of meat reaching the consumer, and additionally may pose health and safety hazards for workers. While cleaning and removal of the dags may be performed at the abattoir before or following slaughter, high microbial loads may be present in dags which may threaten food safety protocols.

Unless otherwise indicated herein, the materials described in this section are not prior art to the claims in this application and are not admitted to be prior art by inclusion in this section.

SUMMARY

Technologies are generally described for a method and composition for managing dag on hair. The presently disclosed method and composition may ease removal of dag from the hair or mitigate dag formation on the hair. For example, hair treated by the presently disclosed method may provide for a lower adherence of dag to hair which may ease the removal of the dag. In addition, mitigating the formation of dag on hair may reduce, or even eliminate, the need to remove the dag. A method and composition for dag management on hair is presently disclosed herein.

In an illustrative method of managing dag on hair, a low energy compound (as defined later in this specification) is applied to the hair. The low energy compound comprises silicone and a terminal reactive group. A hair binding moiety is applied to the hair, wherein the hair binding moiety functionalizes the low energy compound at its terminal reactive group, and enables the functionalized low energy compound to bind to the hair.

In an alternative illustrative method of managing dag on hair a low energy compound selected from the group consisting of mono-aminopropyl terminated polypimethylsiloxane, (3-aminopropyl)tris(trimethylsiloxy) silane, bis(3-aminopropyl) terminated poly(dimethylsiloxane), Mono-(2,3-epoxy)propylether terminated polydimethylsiloxane, and combinations thereof is applied to a container. A hair binding moiety selected from the group consisting of 2-bromohypoxanthine, Lysine hydrochloride, Cysteine, and combinations thereof, is applied to the container. A solvent is added to the container and stirred to form a solution. The solution is applied to the hair to enable ease of removal of dag from the hair or mitigation of dag formation on the hair.

The foregoing summary is illustrative only and is not intended to be in any way limiting. In addition to the illustrative aspects, embodiments, and features described above, further aspects, embodiments, and features will become apparent by reference to the examples and drawings and the following detailed description.

BRIEF DESCRIPTION OF THE FIGURES

The foregoing and other features of this disclosure will become more fully apparent from the following description and appended claims, taken in conjunction with the accompanying drawings and examples. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
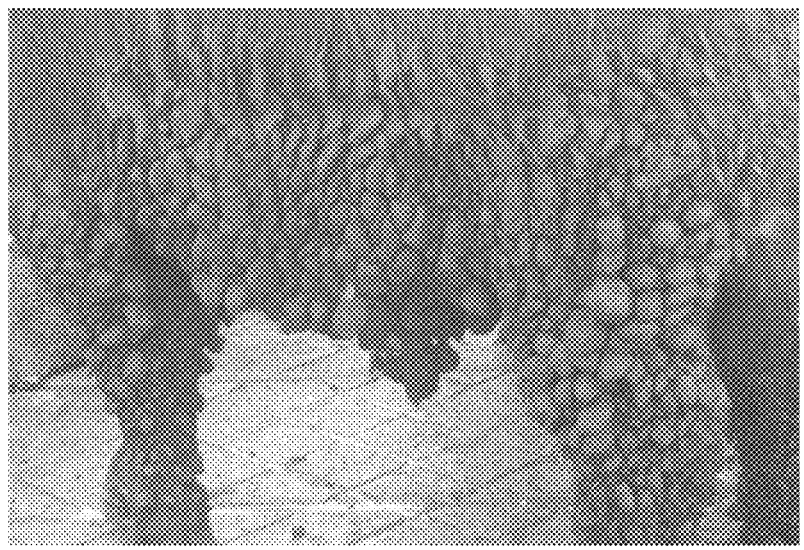
FIG. 1 illustrates an animal having dag on its hair.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This present disclosure addresses issues associated with dag on hair by dag management. This disclosure is generally drawn, inter alia, to methods and compounds for managing dag on hair. Technologies are generally described for a method and compounds, for easing the removal of dag from hair or for reducing, mitigating, or substantially eliminating the formation of dag on hair.

Briefly stated, a method of managing dag on hair includes applying a low energy compound comprising silicone and a terminal reactive group to the hair and applying a hair binding moiety to the hair for functionalizing the low energy compound, at its terminal reactive group; to bind to the hair.

The applied low energy compound enables ease of removal of dag from the hair or mitigation of dag formation on the hair.

As used herein, the term dag means any foreign matter that clings to the skin, hide, hair, wool or other covering of an animal. As used herein, the term functionalized low energy compound means a compound that lowers the surface energy of the hair; that is, the compound leads to a "non-stick" surface on the hair. Thus, dirt, water, dung, and urine may have great difficulty in wetting the surface of the hair having been treated with the presently disclosed method of managing dag on hair. For example, a low energy compound may have a characteristic of decreasing an affinity, or a tendency of formation, of dag on hair. In an illustrative example, the low energy compound of the present disclosure may decrease affinity or strength of adherence or bonding of dag on hair, thus easing the removal of dag from the hair. In at least one other illustrative example, the low energy compound has a hydrophobic portion which may contribute to an ease of removal of dag from the hair or mitigation of dag formation on the hair.

The presently disclosed method and compositions are based upon the functionalized silicones which are safe for human beings, safe for livestock, safe for cattle, and is unlikely to affect beef quality. For example, many silicone materials are used for tissue growth, in food products, and in many personal care, hygiene and cosmetic products.

The silicone materials disclosed herein prevent, or mitigate, dag formation and/or ease the removal of dags from cattle hide or livestock. The presently disclosed method and compounds may be advantageously employed on feedlot-housed live cattle. The silicone materials may be passively used and may not cause stress to animals. For example, the presently disclosed method of managing dag may be performed in concert with other feedlot activities to minimize time spent outside of feeding pens. The presently disclosed method and silicone materials may have little, or no, negative impact on animal welfare, animal safety, worker safety, abattoir meat processing practices, meat safety, meat quality, and/or hide quality. The presently disclosed method and silicone materials may improve public and consumer perceptions of the beef industry by allowing the livestock to be presented in a more visually appealing state. Some of the silicone materials presently disclosed may be common, inexpensive silicone materials that may be scalable for use in large commercial feedlots.

The presently disclosed method provides a silicone material which is functionalized with various moieties. These moieties have structural features that allow the silicone moiety to attach to hair by either polar bonding and/or covalent bonding. The silicone containing low energy compound may reduce the surface energy of the hair, making the hair fibers difficult for the dag and components of the dag to attach to. The dag may have difficulty attaching to the hair of the animal and in this way, it may be, difficult for the dag to grow and may be easier to remove. The presently disclosed functionalized silicone may mitigate dag formation and/or ease the removal of dag.

A method of dag management using functional silicones is presented herein. Silicone materials are commonly used in cosmetic and hair care products under the name dimethicone. They are considered safe to use for these purposes. Silicones are also commonly used for non-stick applications and have been used on the hull of ships to decrease drag. In the present disclosure, the silicone is functionalized with a moiety that allows the silicone to attach, or bind, to hair fibers. The silicone moiety lowers the surface energy of the hair fibers. In effect, a non-stick surface may be applied to the animal's hair. The presently disclosed method and compound may mitigate dag formation and/or make dags easier to remove.

In an illustrative method, a hair binding moiety and a low energy compound comprising silicone and a terminal reactive group are applied to hair. The low energy compound and the hair binding moiety may be applied to the hair separately or together. For example, the low energy compound and the hair binding moiety may first be reacted or linked with each other to form a functionalized low energy compound. The functionalized low energy compound may then be applied to the hair, wherein it is bonded to the hair. Hair treated with the presently disclosed method, or hair having the low energy compound bonded thereto, may mitigate the formation of dag on the treated hair or may improve the removal of dag from the hair.

The term hair is used broadly herein to mean any form of mammalian hair such as wool or any of the fine threadlike strands growing from the skin. The method and constituents of the present disclosure may reduce or even eliminate a need to remove dag from hair and hence keep the hide of cattle substantially free from dag.

As previously explained, for purposes of this disclosure, a dag is considered to be any foreign matter that clings to the skin, hide, hair, wool or other covering of an animal.

The current disclosure may provide a non-stress-inducing method of removing or mitigating the formation of dags. The ease in removal of dags, or mitigation of the formation of dags, may, in turn, mitigate the contamination of the meat. The reduction, mitigation, or elimination of the dags may, in turn, aid the slaughter house in meeting regulations that may require that the cattle be deemed "clean" prior to slaughter.

Silicone materials are common is consumer products. Consumer products ranging from cosmetics to cookware contain silicones. When used in health care, cosmetic, or personal hygiene products, silicones are often called dimethicone. The dimethicone nomenclature comes from the chemical name for silicones which is poly(dimethyl siloxane). Dimethicone is a major component in shampoos and may be added to prevent hair entanglement and matting. However, dimethicone may not adhere or bond to hair and may not manage dag.

The presently disclosed silicone polymers are to be part of a treatment system for livestock. The silicone polymers are functionalized with moieties which allow for their chemical attraction and bonding to hair fibers. The functionalized low energy compounds bond with hair and manage dag on the hair. In at least one illustrative example, the functionalized low energy compound lowers the surface energy of the hair. The lower surface energy leads to a "non-stick" surface on the hair. Thus, dirt, water, dung, and urine may have great difficulty in wetting the surface of the hair having been treated with the presently disclosed method of managing dag on hair.

A wide variety of silicone materials can be used for the presently disclosed method of managing dag on hair. The materials can include both straight chain as well as branched silicones. In at least one embodiment of the present disclosure, a method of managing dag on hair comprises applying a low energy compound comprising silicone and a terminal reactive group to the hair, wherein the silicone is represented by the chemical structure:

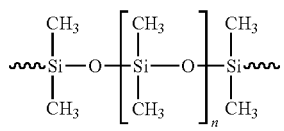

wherein n=10-10.

Terminal reactive groups for attaching the hair binding moieties can be placed on the silicones. Some terminal reactive groups include carboxylic acids, anhydrides, isocyanto, isothiocyanto, thiol, epoxy (oxirane), hydroxyl, amino, acrylic and the like. For example, a low energy compound comprising silicone and a terminal reactive group of the present disclosure may comprise one or more of the compounds listed below:

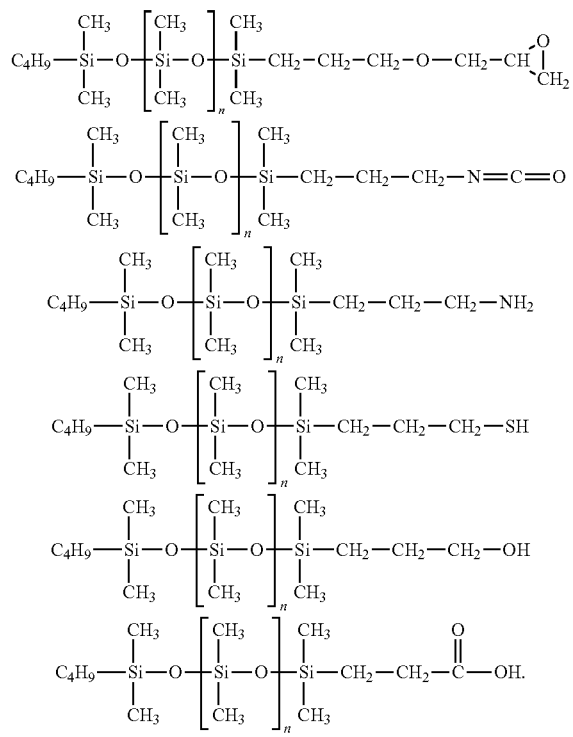

wherein n=10-100.

Terminal active groups that may be a part of the low energy compound comprising silicone may include R—N=C=O, R—OH, R—NH2, R—SH, R—Se, and glycidyl, wherein R is the low energy compound comprising silicone. The low energy compound comprising silicone may have other and additional terminal reactive groups therewith for attaching hair binding moieties thereto, as are known in the art.

The low energy compound comprising silicone and a terminal reactive group may be contacted with a moiety substitution that allows the low energy compound comprising silicone and a terminal reactive group to be chemically bound to the hair. Some hair binding moieties that may interact or bond with hair include thiols, guanine, adenine, thymine, or cytosine, hydroxyl, carboxylic acids, amino acids, polyethers, pyrazole, imidazole, and many other cyclic and chain moieties. For example, one or more of:

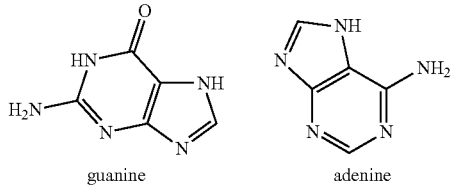

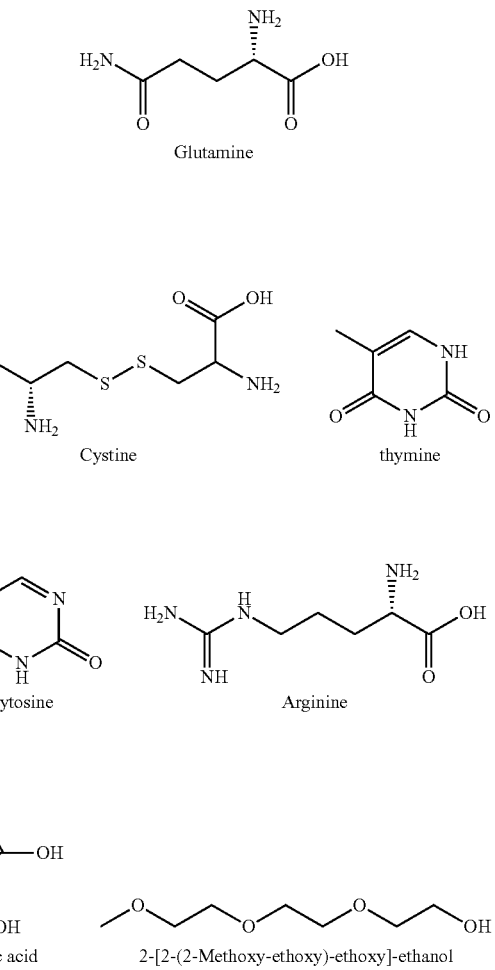

may provide for a hair binding moiety that may be used to functionalize the low energy compound comprising silicone for binding to hair. Some of these hair binding moieties may enable the functionalized the low energy compound comprising silicone to polar bond or covalently bond to hair.

Other and additional hair binding moieties, as known in the art, may be used to functionalize the low energy compound comprising silicone to bind with hair. For example, the hair binding moiety may have one or more of: R'—OH, R'—NH2, R'—XR'—X, R'—X, R'—X, R'—NH2, R'—SH, wherein R' represents a radical and X=Cl, Br, or I.

The functionalized low energy compound comprising silicone may be made by contacting the low energy compound comprising silicone and a terminal reactive group with the hair binding moiety. For example, if urethane and/or urea chemistry is used as the connection point, the resultant may include one or more of:

Silicone    Hair Treatment
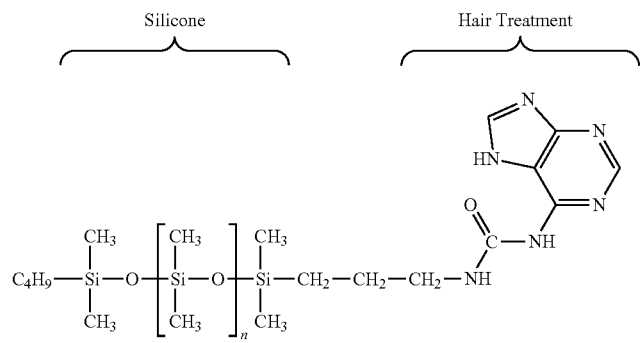
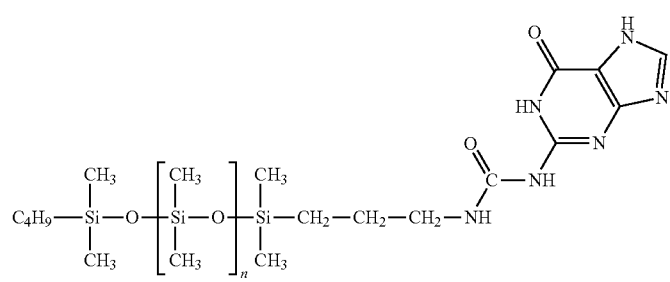
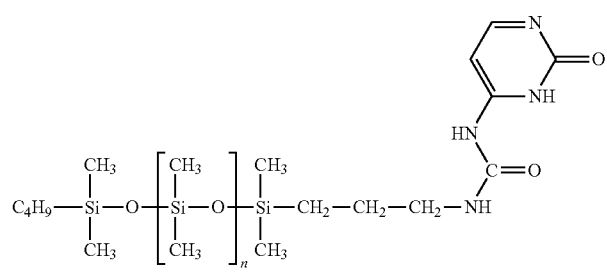
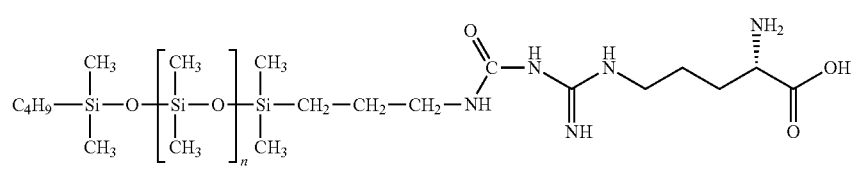
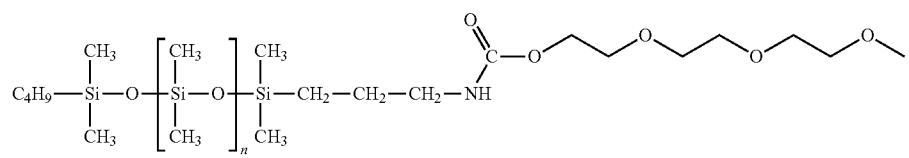
wherein n=10-100.

The functionalized low energy compound comprising silicone may be DNA based. In at least one illustrative example, the functionalized low energy compound may be represented by one or more of the following structures:

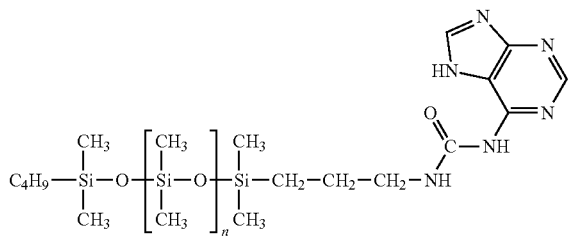

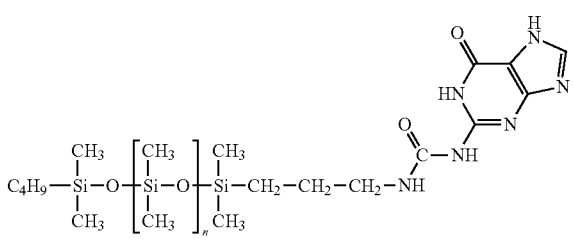

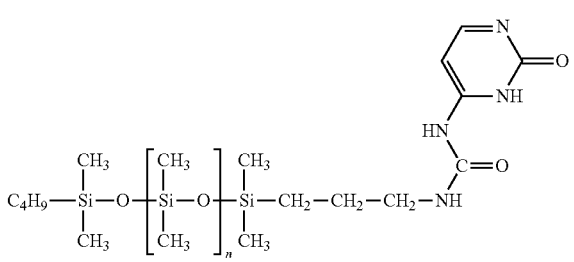

Other low energy compounds comprising silicone and a terminal reactive group may be contacted with other hair binding moieties, such as an epoxy moiety. If epoxy is used as the hair binding moiety, the resulting functionalized low energy compound may have a different connection point between the silicone and the hair attractive moieties, but the overall properties of attaching to hair and managing dag may remain the same. For example, a longer hydrophilic or hydrophobic entity may be placed between the hair treatment group, or hair binding constituent, and the silicone.

The functionalized low energy compound comprising silicone may be referred to as a functionalized silicone resin. The silicone portion may provide for a non-stick surface whereas the functional moiety may provide for bonding to hair fibers. For example, the functionalized low energy compound comprising silicone obtained by contacting the low energy compound comprising silicone and a terminal reactive group with a hair binding agent may be applied to the hair of livestock. Application to livestock may be accomplished in many ways. Some application methods include neat, dissolving into zero-VOC solvents such as acetone or other organic media, supercritical fluids such as carbon dioxide or argon, or on various powders or support media. A practical method may include formulation into a shampoo. In a shampoo, the functionalized silicone materials may be dispersed in a water media. The water media may be applied to the animal and then rinsed off.

EXAMPLES

Example 1

A solution of 2-bromohypoxanthine (Aldrich, 10.0 g, 46.5 mmol) in methanol (200 mL) is added mono-aminopropyl terminated polypimethylsiloxane (Gelest, 30.69 g, 93.0 mmol) and diisopropylethylamine (20.2 mL, 116.3 mmol). The reaction is stirred at 90° C. overnight. The solvent is removed by rotary evaporation and the remaining fluid is collected. The fluid is purified by column chromatography using methylene chloride:methanol (98:2) on silica which separates the remaining mono-aminopropyl terminated polypimethylsiloxane and the desired product. The desired product comprises a functionalized low energy compound comprising silicone and a terminal reactive group.

Example 2

To a solution of 2-bromohypoxanthine (Aldrich, 10.0 g, 46.5 mmol) in methanol (200 mL) is added (3-aminopropyl)tris(trimethylsiloxy)silane (Aldrich, 32.90 g, 93.0 mmol) and diisopropylethylamine (20.2 mL, 116.3 mmol). The reaction is stirred at 90° C. overnight. The reaction may be represented by:

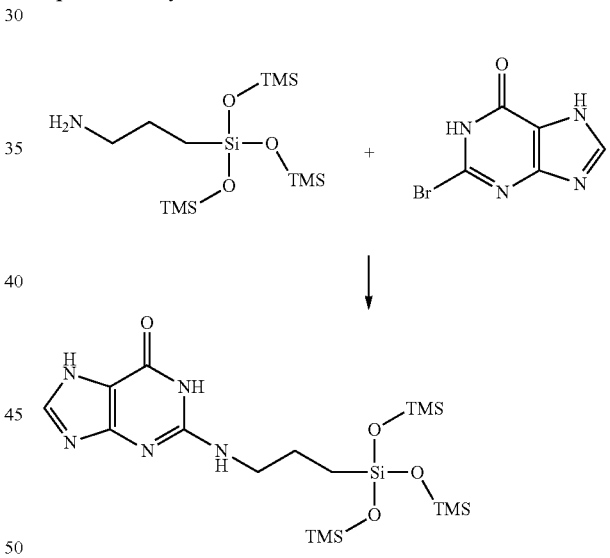

The solvent is removed by rotary evaporation and the remaining fluid is collected. The fluid is purified by column chromatography using methylene chloride: methanol (98:2) on silica which separated the remaining (3-aminopropyl)tris(trimethylsiloxy)silane and the desired product. The desired product comprises a functionalized low energy compound comprising silicone and a terminal reactive group.

Example 3

To a solution of 2-bromohypoxanthine (Aldrich, 10.0 g, 46.5 mmol) in methanol (200 mL) is added poly(dimethylsiloxane), bis(3-aminopropyl) terminated (Gelest, 88.35 g, 93.0 mmol) and diisopropylethylamine (20.2 mL, 116.3 mmol). The reaction is stirred at 90° C. overnight. The reaction may be represented by:

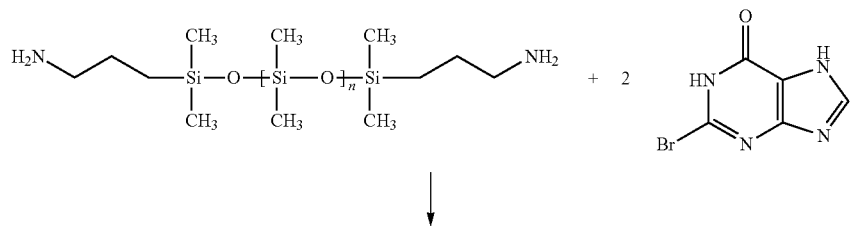

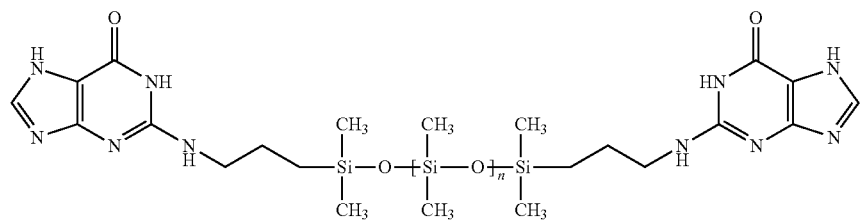

The solvent is removed by rotary evaporation and the remaining fluid was collected. The fluid is purified by column chromatography using methylene chloride:methanol (98:2) on silica which separated the remaining bis-aminopropyl terminated polypimethylsiloxane and the desired product. The desired product comprises a functionalized low energy compound comprising silicone and a terminal reactive group.

Example 4

To a solution of 2-bromohypoxanthine (Aldrich, 10.0 g, 46.5 mmol) in methanol (200 mL) is added poly(dimethylsiloxane), bis(3-mercaptopropyl) terminated (Genesee, 450 g, ~93.0 mmol) and diisopropylethylamine (20.2 mL, 116.3 mmol). The reaction is stirred at 90° C. overnight. The reaction may be represented by:

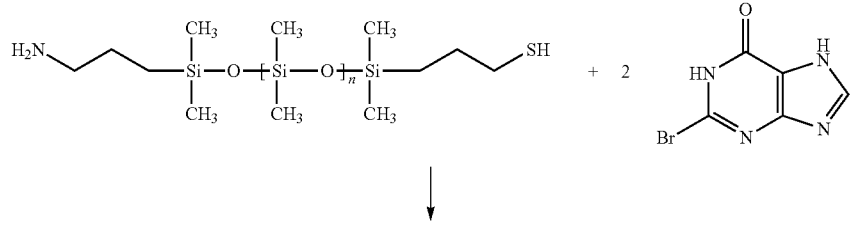

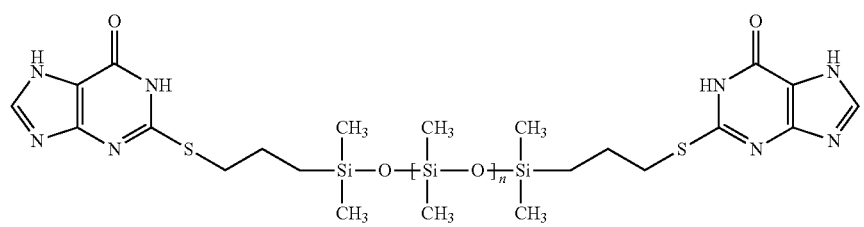

The solvent is removed by rotary evaporation and the remaining fluid is collected. The fluid is purified by column chromatography using methylene chloride:methanol (98:2) on silica which separated the remaining bis-mercaptopropyl terminated polypimethylsiloxane and the desired product. The desired product comprises a functionalized low energy compound comprising silicone and a terminal reactive group.

Example 5

Lysine hydrochloride (Aldrich, 10 g, 54.75 mmol) is dissolved into 100 mL of water. Mono-(2,3-epoxy)propylether terminated polydimethylsiloxane (Gelest, 54.75 g, 54.75 mmol) is dissolved into toluene (100 mL). The toluene solution and water solutions are combined and stirred rapidly together followed by heating to 40-130° C. The reaction may be represented by:

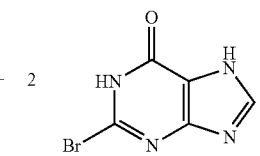

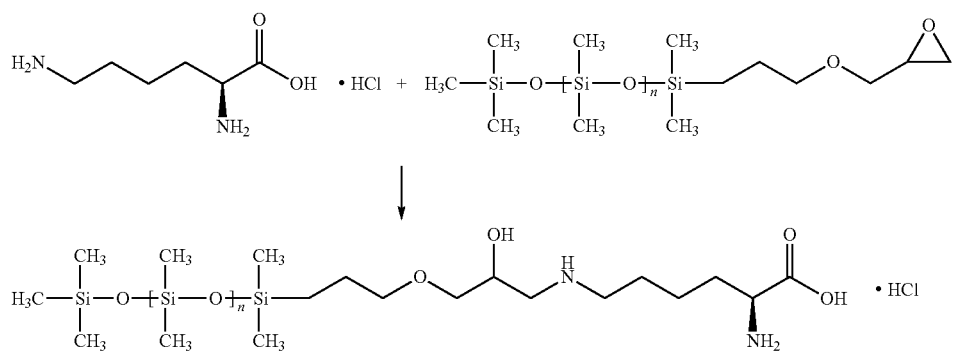

The water and toluene are removed by rotary evaporation to yield a viscous cloudy oil. The oil is loaded onto a silica column and purified using methylene chloride:methanol (98:2) to yield a mixture of lysine hydrochloride grafted by polydimethyl siloxane on the 2-position nitrogen and 6-position nitrogen. This desired product comprises a functionalized low energy compound comprising silicone and a terminal reactive group.

Example 6

Cysteine (reduced form, Aldrich, 10 g, 82.54 mmol) is dissolved into 100 mL of water. Mono-(2,3-epoxy)propyl-ether terminated polydimethylsiloxane (Gelest, 82.54 g, 82.54 mmol) is dissolved into toluene (150 mL). The toluene solution and water solutions are combined and stirred rapidly together followed by heating to 40-130° C. The reaction may be represented by:

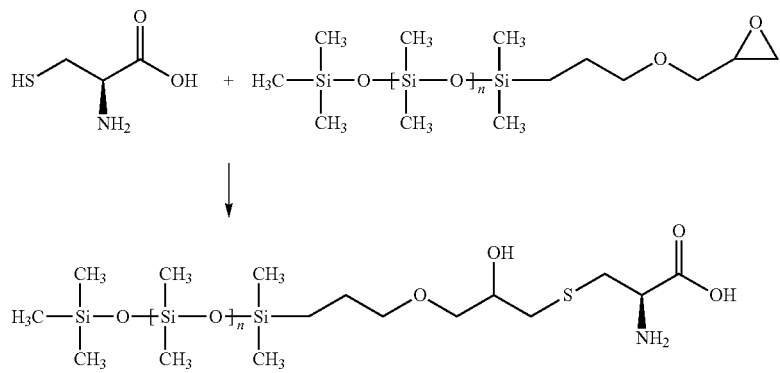

The water and toluene are removed by rotary evaporation to yield a viscous cloudy oil. The oil is loaded onto a silica column and purified using methylene chloride:methanol (98:2) to yield a mixture of cysteine grafted by polydimethyl siloxane on the sulfur and minor nitrogen. This desired product comprises a functionalized low energy compound comprising silicone and a terminal reactive group.

Example 7

50 g of the product obtained in Example 2 is dissolved into 50 g of acetone. The solution is placed into a high speed disperser equipped with vacuum system and addition funnel. The temperature is set to 30° C. Deionized water is added to the addition funnel. Water, 150 mL, is added at 10,000 rpm. Vacuum (740 torr) is then placed on the system and gradually increased until 150 torr over a 90 minute period until all the acetone is removed and collected by cold trap. The stir rate is maintained at 10,000 rpm. The vacuum is released once the acetone is removed and a translucent mixture results. The water solution or translucent mixture may then be applied to the hair.

The low energy compound and hair binding moiety may be applied onto the hair, or mixed together, at an equivalent ratio to provide for the functionalized low energy compound for curing and bonding to the hair.

Figure 2:
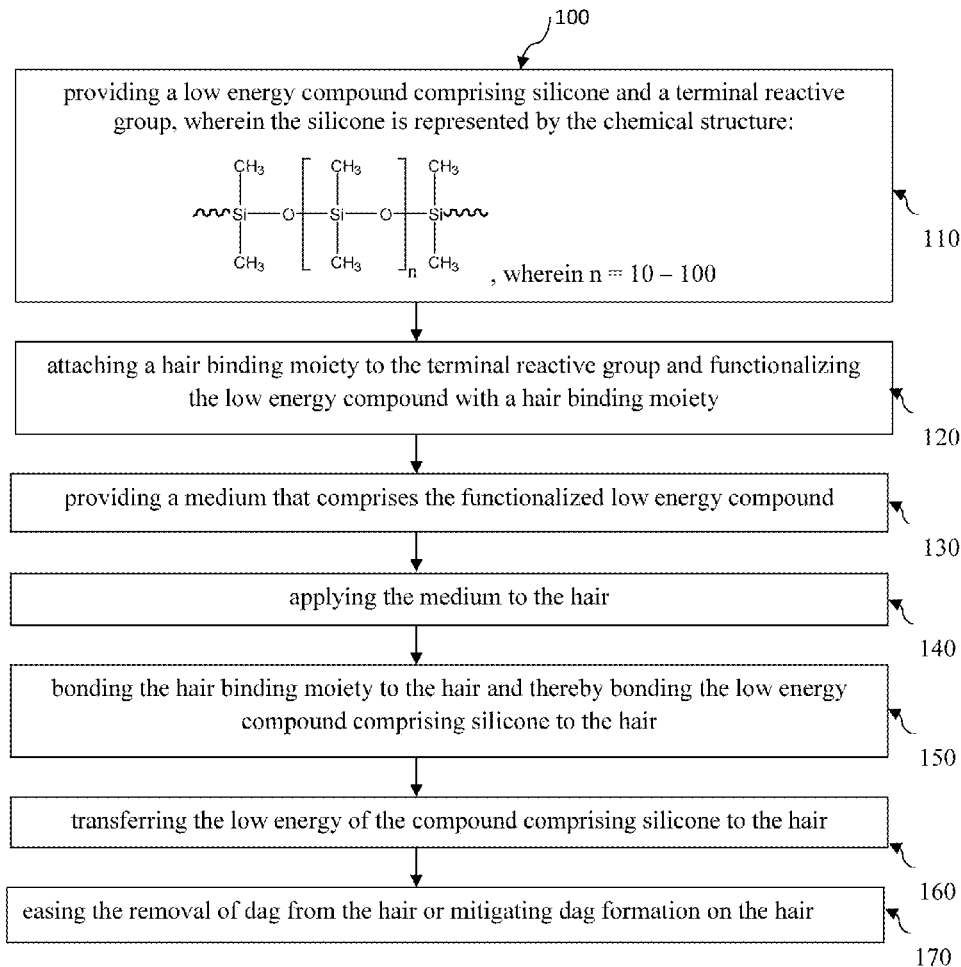
FIG. 2 illustrates a flow chart of a method of managing dag on hair of the present disclosure.

FIG. 2 shows an illustrative method 100 of managing dag on hair of the present disclosure. In step 110 a low energy compound comprising silicone and a terminal reactive group is provided. The silicone is represented by the chemical structure:

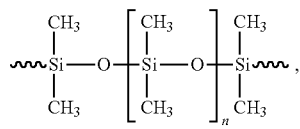

wherein n=10-100.

In step 120, a hair binding moiety is attached to the terminal reactive group which functionalizes the low energy compound with a hair binding moiety. A medium may be provided for application of the functionalized low energy compound comprising silicone to hair in step 130. Step 130 may be optional as the functionalized low energy compound comprising silicone may be applied directly to hair. In at least one embodiment, the medium is a liquid, such as water or a shampoo.

At step 140 the medium is applied to hair being treated. The application may be done by simply spraying the medium onto the hair. For example, in an illustrative method, a medium having a functionalized low energy compound is in liquid form and the step of applying the medium to the hair 140 may include spraying, rinsing, dispersing, or applying by means which are known by persons having ordinary skill in the art for applying a liquid to hair. However, it is to be understood that one or more of the low energy compound, hair binding moiety, functionalized low energy compound, or medium may be in solid or powder form and the step of applying to the hair may include dusting, sprinkling, or applying by means which are known by persons having ordinary skill in the art for applying a solid or powder to hair. Additionally, step 120 may be performed insitu on the hair and the hair binding moiety and low energy compound may be applied separately or together.

Upon having the functionalized low energy compound applied to the hair at step 140, bonding of the moiety to the hair occurs, which bonds the low energy compound comprising silicone to the hair at step 150. Thus, the low energy of the compound comprising silicone is transferred to the hair at step 160 and easing the removal of dag from the hair or mitigating dag formation on the hair is achieved at step 170.

Examples of the presently disclosed method of managing dag on hair by applying a low energy compound comprising silicone and a terminal reactive group to the hair and applying a hair binding moiety to the hair are represented in Table 1.

TABLE 1

| 1. Silicone Functional Group, or low energy compound comprising silicone and a terminal reactive group | 2. Substrate Functional Group, or hair binding moiety | 3. Linkage between the low energy compound comprising silicone and the hair binding moiety, or functionalized low energy compound |
|---|---|---|
| R—N=C=O | R'—OH | R—NH—C(=O)—O—R' |
| R—N=C=O | R'—NH2 | R—NH—C(=O)—NH—R' |
| R—OH | R'—X (X=Cl, Br, I) | R—O—R' |
| R—NH2 | R'—X (X=Cl, Br, I) | R—NH—R' |
| R—SH | R'—X (X=Cl, Br, I) | R—S—R' |
| R—Se | R'—X (X=Cl, Br, I) | R—Se—R' |
| glycidyl | R'—NH2 | R—CH2—CH(OH)-CH2—NH—R' |
| glycidyl | R'—SH | R—CH2—CH(OH)-CH2—S—R' | wherein R is a low energy compound comprising silicone and R' is a radical on the hair binding moiety.

Table 1 shows a linkage, shown in column 3, that may be made between a selected low energy compound comprising silicone and a terminal reactive group, shown in column 1, and a selected hair binding moiety, shown in column 2. For example, row 1 shows that R—N=C=O may react with R'—OH to yield R—NH—C(=O)—O—R', which may be applied to hair to manage dag. In some illustrative examples of the presently disclosed method, the low energy compound and hair binding moiety may be applied to hair separately and a reaction may take place in situ on the hair. In some examples, a reaction between the hair binding moiety and the low energy compound may take place prior to an application to the hair.

Additional materials may also be applied to the hair. For example, one or more hardeners, catalysts, solvents, or other materials may be applied to the hair which may enhance, speed up, or drive a bonding reaction which may hold the low energy compound to the hair. One or more of these materials may be applied to the hair, or mixed with one or both of the low energy compound and hair binding moiety, at desired equivalent ratio.

There is thus provided a method of managing dag on hair. The present disclosure may provide a new method of improving the removal of dags or mitigating or preventing dags to be formed on the hides of the live cattle as a non-stress-inducing method. The method may provide for an application to live cattle before the wet winter months, for example. The presently disclosed method may not involve activities and factors that are known to be stressful to cattle such as noisy environment, electric prodding, brushing, and shearing.

The presently disclosed method may have widespread applications. For example, global beef consumption may be on the order of 62 million tons carcass weight equivalent (tcwe) annually. This refers to the weight of dressed carcass. For example, in Australia, the number of cattle slaughtered in 2013 was estimated at 8.4 million head, amounting to 1.84 million tcwe. Of these, 2.9 million head were grain fed. The Australian national cattle herd was 28.25 million head in 2013. Of these, almost 14 million head were in southern Australia. Australia is known to have cattle with dags and the presently disclosed method may aid in managing dag and the problems associated therewith.

In an illustrative method, a method of managing dag on hair comprises applying a low energy compound comprising silicone and a terminal reactive group to the hair, wherein the silicone is represented by the chemical structure:

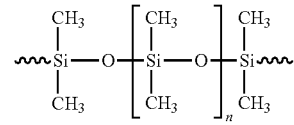

wherein n=10-100.

A hair binding moiety is applied to the hair for functionalizing the low energy compound, at its terminal reactive group, and thereby binding the functionalized low energy compound to the hair and enabling ease of removal of dag from the hair or mitigation of dag formation on the hair. The low energy compound may be functionalized prior to being applied to the hair. The low energy compound may be mixed with the hair binding moiety to form a solution and the solution may be applied to the hair. For example, the solution may be sprayed onto the hair. The solution may be a shampoo, an aqueous solution, or an organic solvent solution. The low energy compound may be a powder which may be applied to the hair.

The low energy compound may be selected from the group consisting of:

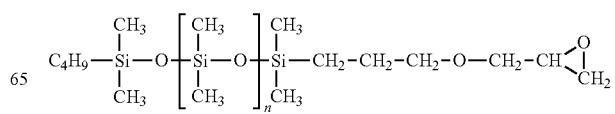

-continued

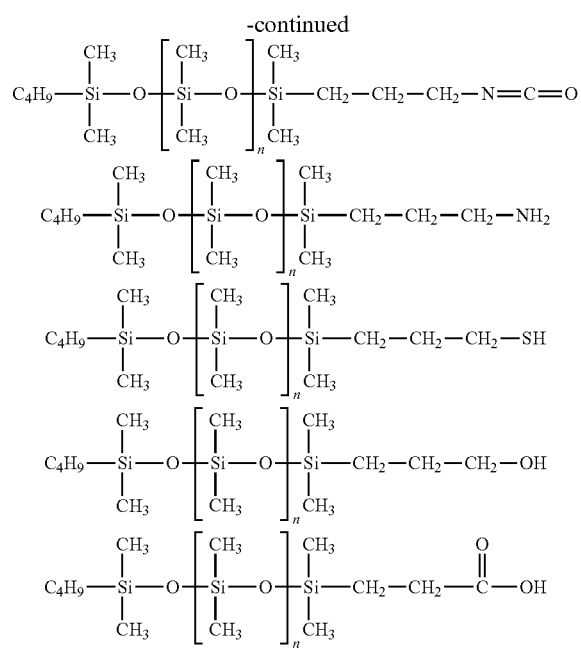

and combinations thereof; wherein n=10-100.

The terminal reactive group may be selected from the group consisting of carboxylic acids, anhydrides, isocyanto, isothiocyanto, thiol, epoxy, hydroxyl, amino, acrylic, and combinations thereof. The terminal reactive group on the low energy compound may be selected from the group consisting of: R—N=C=O, R—OH, R—NH2, R—SH, R—Se, glycidyl, and combinations thereof; wherein R is the low energy compound comprising silicone.

The hair binding moiety may be selected from the group consisting of:

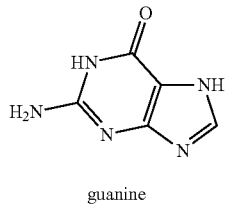
guanine

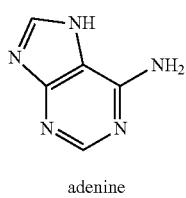
adenine

-continued

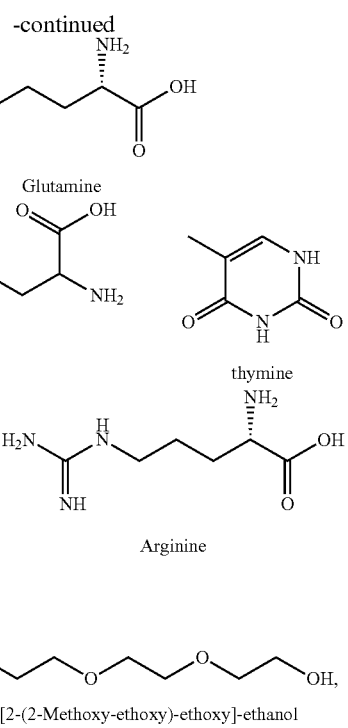

and combinations thereof.

The hair binding moiety may be selected from the group consisting of thiols, guanine, adenine, thymine, cytosine, hydroxyl, carboxylic acids, amino acids, polyethers, pyrazole, imidazole, cyclic and chain moieties, and combinations thereof, or the group consisting of R'—OH, R'—NH2, R'—XR'—X, R'—X, R'—X, R'—NH2, R'—SH, and combinations thereof; wherein R' represents a radical and X=Cl, Br, or I.

The functionalized low energy compound may include a linkage between the low energy compound and the hair binding moiety selected from the group consisting of R—NH—C(=O)—O—R', R—NH—C(=O)—NH—R', R—O—R', R—NH—R', R—S—R', R—Se—R', R—CH2-CH(OH)—CH2-NH—R', R—CH2-CH(OH)—CH2-S—R', and combinations thereof; and wherein R is the low energy compound comprising silicone and R' represents a radical on the hair binding moiety.

The functionalized low energy compound may be selected from the group consisting of:

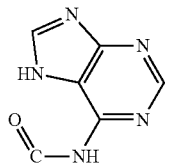

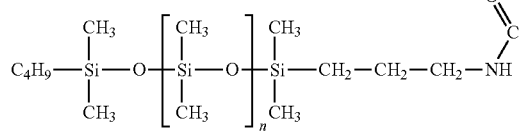

-continued

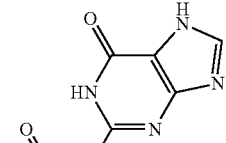
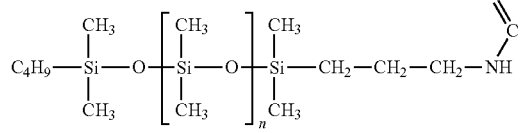

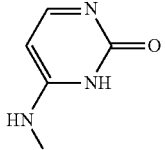
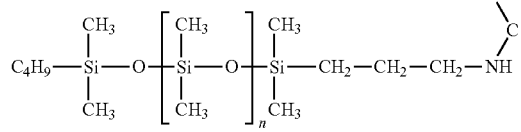

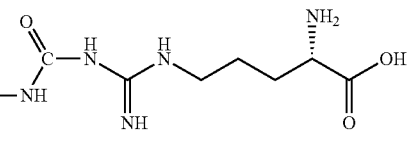
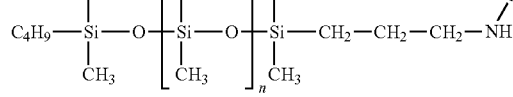

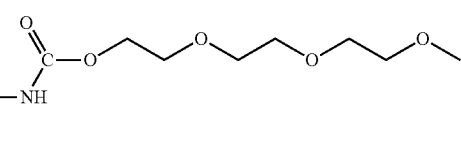
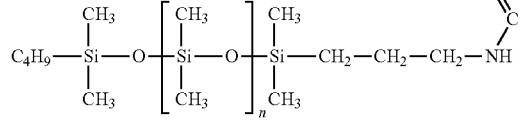

and combinations thereof;
or may be selected from the group consisting of:

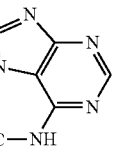
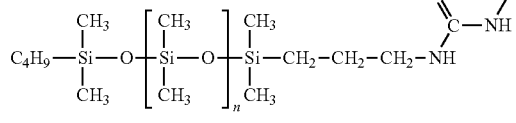

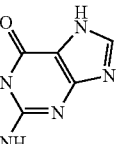
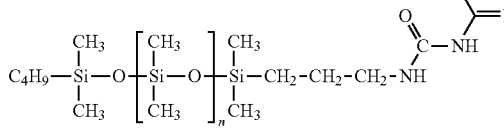

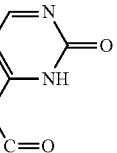
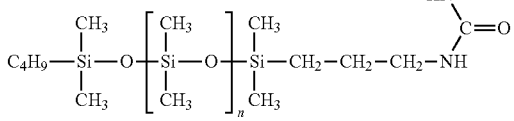

and combinations
wherein n=10-100.

An illustrative method of managing dag on hair may include: adding a low energy compound selected from the group consisting of mono-aminopropyl terminated polypimethylsiloxane, (3-aminopropyl)tris(trimethylsiloxy) silane, bis(3-aminopropyl) terminated poly(dimethylsiloxane), Mono-(2,3-epoxy)propylether terminated polydimethylsiloxane, and combinations thereof, to a container; adding a hair binding moiety selected from the group consisting of 2-bromohypoxanthine, Lysine hydrochloride, Cysteine, and combinations thereof, to the container; adding a solvent to the container and stirring to form a solution; and applying the solution to the hair and thereby managing the dag on the hair. The method may further include adding diisopropylethylamine to the solution. The solvent may include at least one of methanol, water, and toluene. The method may further include separating a functionalized low energy compound from the solution, performed prior to applying the solution to the hair. The separation of the functionalized low energy compound from the solution may include evaporating the solvent from the solution.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of managing dag formation on hair, the method comprising:
applying a low energy compound to the hair, wherein the low energy compound comprises silicone and a terminal reactive group, wherein the silicone is represented by the chemical structure:

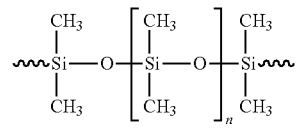

wherein n=10-100;
applying a hair binding moiety to the hair, wherein the hair binding moiety functionalizes the low energy compound at its terminal reactive group, and enables the functionalized low energy compound to bind to the hair, and wherein the hair binding moiety is R'—X, wherein R' represents hypoxanthine and X=Br.

2. The method of claim 1, wherein the applying a low energy compound comprises applying a powder to the hair.

3. The method of claim 1, wherein the low energy compound is:

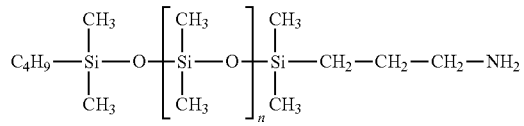

wherein n=10-100.

4. The method of claim 1, wherein the terminal reactive group is amino.

5. The method of claim 1, wherein terminal reactive group is R—NH$_2$, wherein R is the low energy compound comprising silicone.

6. The method of claim 1, wherein the functionalized low energy compound comprises a linkage between the low energy compound and the hair binding moiety, R—NH—C(=O)—NH—R' wherein R is the low energy compound comprising silicone and R' represents hypoxanthine.

7. The method of claim 1, wherein the functionalized low energy compound is:

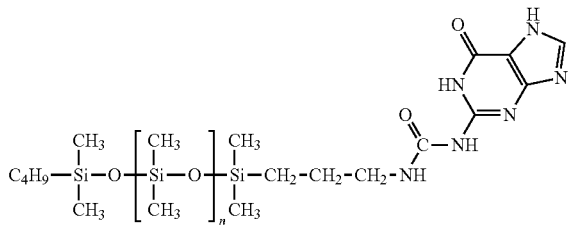

wherein n=10-100.

8. The method of claim 1, wherein the functionalized low energy compound is selected from the group consisting of:

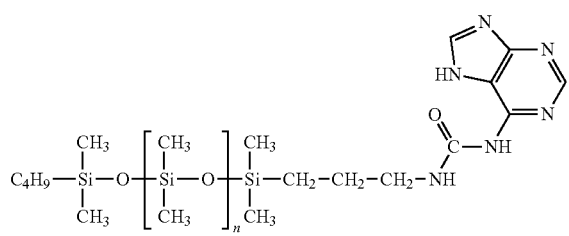

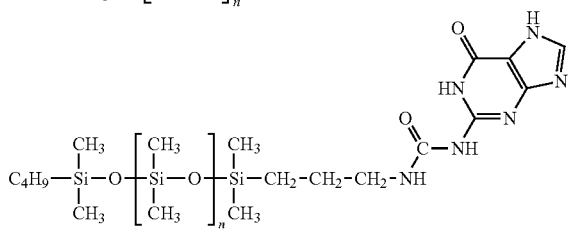

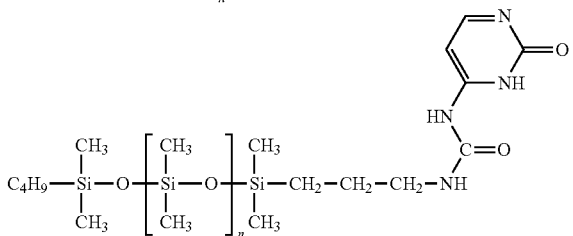

wherein n=10-100.

9. The method of claim 1, wherein the binding the functionalized low energy compound to the hair comprises polar or covalently bonding the hair binding moiety to the hair.

10. A method of managing dag on hair comprising:
adding a low energy compound mono-aminopropyl terminated poly dimethylsiloxane, to a container;
adding a hair binding moiety, 2-bromohypoxanthine to the container;
adding a solvent to the container and stirring to form a solution; and
applying the solution to the hair to enable ease of removal of dag from the hair or mitigation of dag formation on the hair.

11. The method of claim 10, further comprising adding diisopropylethylamine to the solution.

12. The method of claim 10, wherein the solvent comprises at least one of methanol, water, and toluene.

13. The method of claim 10, further comprising separating a functionalized low energy compound from the solution, performed prior to applying the solution to the hair.

14. The method of claim 13, wherein separating a functionalized low energy compound from the solution comprises evaporating the solvent from the solution.

15. A method of managing dag formation on hair, the method comprising:
mixing a low energy compound with a hair binding moiety to form a solution, and applying the solution to the hair, wherein the low energy compound comprises silicone and a terminal reactive group, wherein the silicone is represented by the chemical structure:

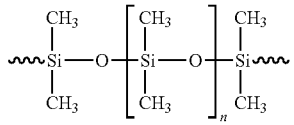

wherein n=10-100;
wherein the hair binding moiety functionalizes the low energy compound at its terminal reactive group, and enables the functionalized low energy compound to bind to the hair; and wherein the hair binding moiety is R'—X, wherein R' represents hypoxanthine and X=Br.

16. The method of claim 15, wherein the applying the solution to the hair comprises spraying the solution onto the hair.

17. The method of claim 15, wherein the solution is a shampoo, an aqueous solution, or an organic solvent solution.

* * * * *

UNITED STATES PATENT AND TRADEMARK OFFICE
CERTIFICATE OF CORRECTION

PATENT NO. : 9,789,054 B1
APPLICATION NO. : 15/170923
DATED : October 17, 2017
INVENTOR(S) : Phelan et al.

Page 1 of 1

It is certified that error appears in the above-identified patent and that said Letters Patent is hereby corrected as shown below:

In the Specification

In Column 6, Line 35, delete "  " and insert -- 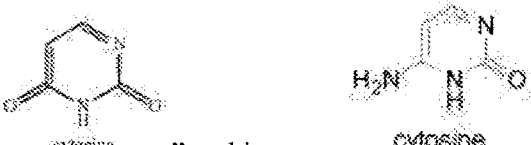 --, therefor.

Signed and Sealed this
Ninth Day of January, 2018

Joseph Matal
*Performing the Functions and Duties of the
Under Secretary of Commerce for Intellectual Property and
Director of the United States Patent and Trademark Office*